United States Patent [19]
Seigel et al.

[11] Patent Number: 5,431,154
[45] Date of Patent: Jul. 11, 1995

[54] INCENTIVE METERED DOSE INHALER

[76] Inventors: David Seigel, 8341 DeSoto Ave., #22, Canoga Park, Calif. 91304; Dennis H. Ware, Sr., 11234 Sunburst St., Lakeview Terrace, Calif. 91342; George Torres, 1016 S. Ashford Ct., Westlake Village, Calif. 91361

[21] Appl. No.: 48,966

[22] Filed: Apr. 16, 1993

Related U.S. Application Data

[63] Continuation of Ser. No. 800,380, Nov. 29, 1991, abandoned.

[51] Int. Cl.⁶ .................................. A61M 11/00
[52] U.S. Cl. ......................... 128/200.14; 128/200.23; 128/727
[58] Field of Search ............. 128/200.14, 200.23, 128/203.12, 727

[56] References Cited

U.S. PATENT DOCUMENTS

| | | | |
|---|---|---|---|
| 4,171,804 | 10/1979 | Thead, Jr. | 128/727 |
| 4,210,155 | 7/1980 | Grimes | 128/727 |
| 4,284,083 | 8/1981 | Lester | 128/727 |
| 4,391,283 | 7/1983 | Sharpless et al. | 128/727 |
| 4,425,923 | 1/1984 | Gordon et al. | 128/727 |
| 4,938,210 | 7/1990 | Shene | 128/200.23 |
| 4,984,158 | 1/1991 | Hillsman | 128/725 |

*Primary Examiner*—Edgar S. Burr
*Assistant Examiner*—Aaron J. Lewis
*Attorney, Agent, or Firm*—Robbins, Berliner & Carson

[57] ABSTRACT

An inhalation device for administering an aerosolized medication includes an incentive spirometer and a medication inhalation chamber having receptacle means adapted to receive a metered dose inhaler for misting aerosolized medication in the chamber. Further provided is a method for administering an aerosolized medication which involves training a subject to breath using the inhalation device and administration of the medication from the device.

25 Claims, 2 Drawing Sheets

INCENTIVE METERED DOSE INHALER

This is a continuation of application Ser. No. 07/800,380, filed on Nov. 29, 1991, now abandoned.

BACKGROUND OF THE INVENTION

1. Field of the Invention

The present invention relates generally to inhalation therapy devices, and more particularly to an inhalation device which provides an incentive spirometer coupled with a metered dose inhaler (MDI) for delivering an aerosolized medication to the respiratory system.

2. Description of Related Art

The publications and other reference materials referred to herein to describe the background of the invention and to provide additional detail regarding its practice are hereby incorporated by reference.

Individuals afflicted with diseases which compromise lung function such as asthma, bronchitis, emphysema, and the like are most commonly treated by oral or aerosolized inhaled bronchodilators. Bronchodilators, anti-inflammatory agents, decongestants and other such medicines are commonly prescribed using MDI-type devices. It has been shown that MDI is a superior method of aerosol administration because the small and uniformed size of the aerosolized medication particles more effectively penetrates to the smaller branches of the bronchi.

Recent studies, have shown, however, that about 10% to 20% of patients taking MDI treatment fail to receive optimal aerosol deposition because improper or poor inhalation technique. Poor inhalation technique is generally due to inadequate inspirations, faulty timing, as well as misunderstood directions. For example, patients have difficulty using conventional MDI devices because they fail to precisely time the activation of the MDI with inhalation. Sometimes patients will inhale too quickly or neglect to hold their breath for a brief period of time in order to insure that the aerosolized medication will be sufficiently deposited into the airways.

The desired time interval of breath holding time is approximately 10 seconds, as discussed in "An Evaluation of Incentive Spirometry For Bronchodilator Therapy" (Frost, G., RRT., Vol. 24, Issue 5, p.11, 1988). It has also been proposed that a brief exhalation, followed by a slow, sustained inhalation will yield the most favorable results in terms of improved bronchodilation. Incentive spirometers, like the DHD Coach ™ Model 22-4000 (DHD Medical Products Company) with a feedback device, are particularly useful because they train patients to inhale slowly, maximally, and hold the full breath. Such breath control enhances the patient's ability to receive optimal delivery of medication to the bronchial airways.

Examples of devices using, in combination, a small volume nebulizer and an inhalation aid, such as a spirometer, for monitoring and measuring a patient's inspiration volume and airflow rate are shown in U.S. Pat. Nos. 4,114,608, 4,259,951, 4,809,706 and 4,984,158. The devices disclosed in the aforesaid patents teach patients how to exercise and/or monitor his or her lungs while used in cooperation with a medication that can be inspired. However, none of these devices alleviate the difficulty of precisely timing manual activation of the MDI with inspiration because they do not allow the aerosilized medication to be held in suspension prior to delivery. Furthermore, these devices have the disadvantage of permitting large, untherapeutic droplets, rather than smaller, thereapeutic particles of medication to be delivered to the airways.

Accordingly, there is a need for a device which provides a simple and inexpensive way to deliver an aerosolized medication, where optimal aerosol particle deposition and particle size is achieved, and which coaches the patient to achieve slow-flow inspiration and adequate breath holding, and which alleviates the need for precise timing of manual activation of an MDI with inhalation.

Without proper delivery and deposition of aerosolized medication particles throughout the bronchial airways, the patient most likely will derive little or no benefit from this form of therapy.

SUMMARY OF THE INVENTION

In accordance with the present invention there is provided an inhalation device for respiratory care which overcomes the above-mentioned problems and provides a new and improved way to deliver aerosolized medication, such as a bronchodilator, from MDI devices.

The device provides the advantages of coaching the patient into taking a slow, inspiratory flow; measurng the volume of the flow; eliminating large, untherapeutic particles of medication from the stream of delivery into the patient's airways, achieving the delivery of small particle aerosolized medication to the airways for therapeutic deposition thereon, and eliminating the problem of precise timing of inspiration with manual activation of the metered dose inhaler (MDI) cannister.

The device of the present invention comprises the unique combination of an incentive spirometer, which is a lung volume exercising apparatus, with a medication inhalation chamber. In a preferred version of the invention, the chamber has a substantially cylindrical shape. The chamber has receptacle means which opens into the chamber. The receptacle means is adapted to receive a metered dose inhaler (MDI) cannister for misting aerosol medication into the medication inhalation chamber. The medication inhalation chamber is placed in-line with the incentive spirometer. The device further comprises an elongated hose having a mouthpiece downstream and coupling means at its upstream end for in-line connection with said medication inhalation chamber.

The present invention further provides a method for administering an aerosolized medication to a subject. This method comprises the steps of providing an inhalation device, as described above, which comprises an incentive spirometer coupled in line with a medication inhaler chamber and an elongate hose having a mouthpiece. The method further involves training the subject with the device to achieve desired breathing parameters, actuating the metered dose inhaler to mist the aerosolized medication into the chamber, and the subject inspiring the aerosolized medication to achieve therapeutic deposition of the medication in the airways.

The above discussed and many other advantages and features of the present invention will become readily apparent as the invention is better understood by reference to the following detailed description and from the accompanying drawings.

DETAILED DESCRIPTION OF THE INVENTION

Figure 1:
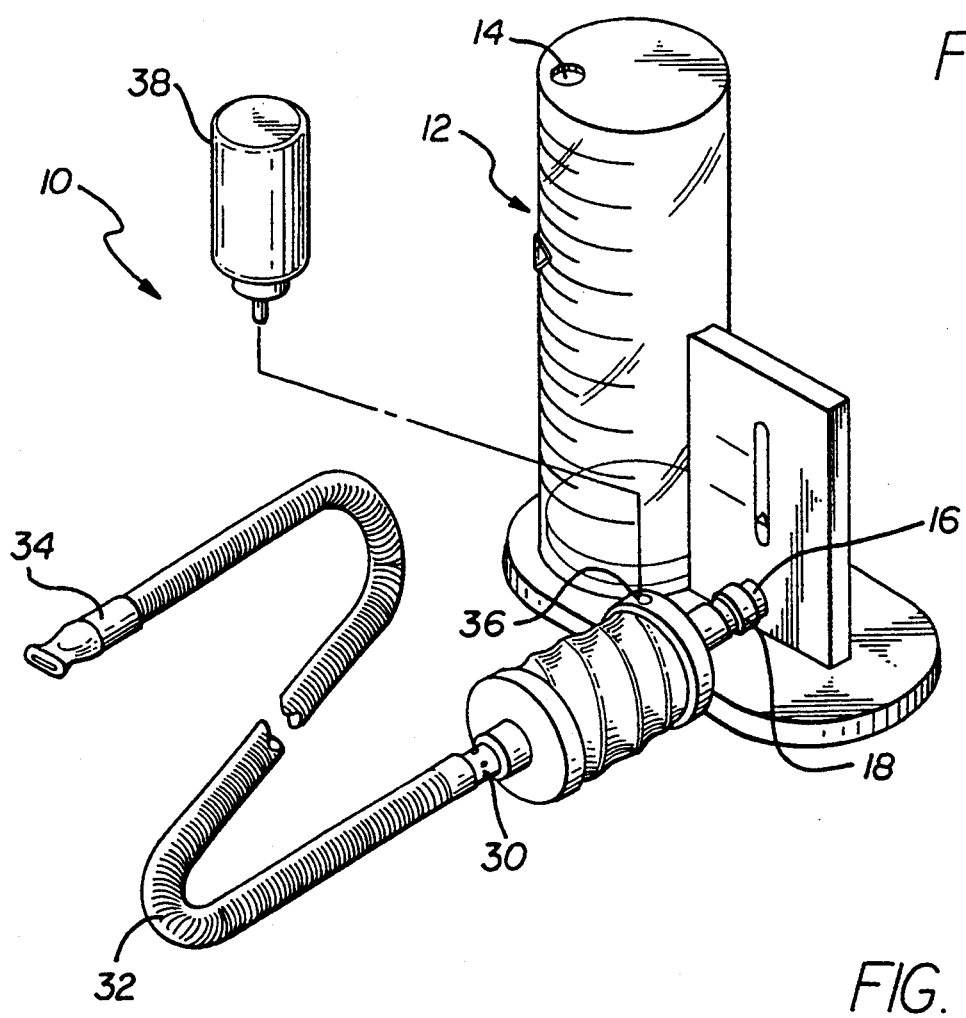
FIG. 1 is a perspective view of the inhalation device for respiratory care constructed in accordance with the present invention.
Figure 2:
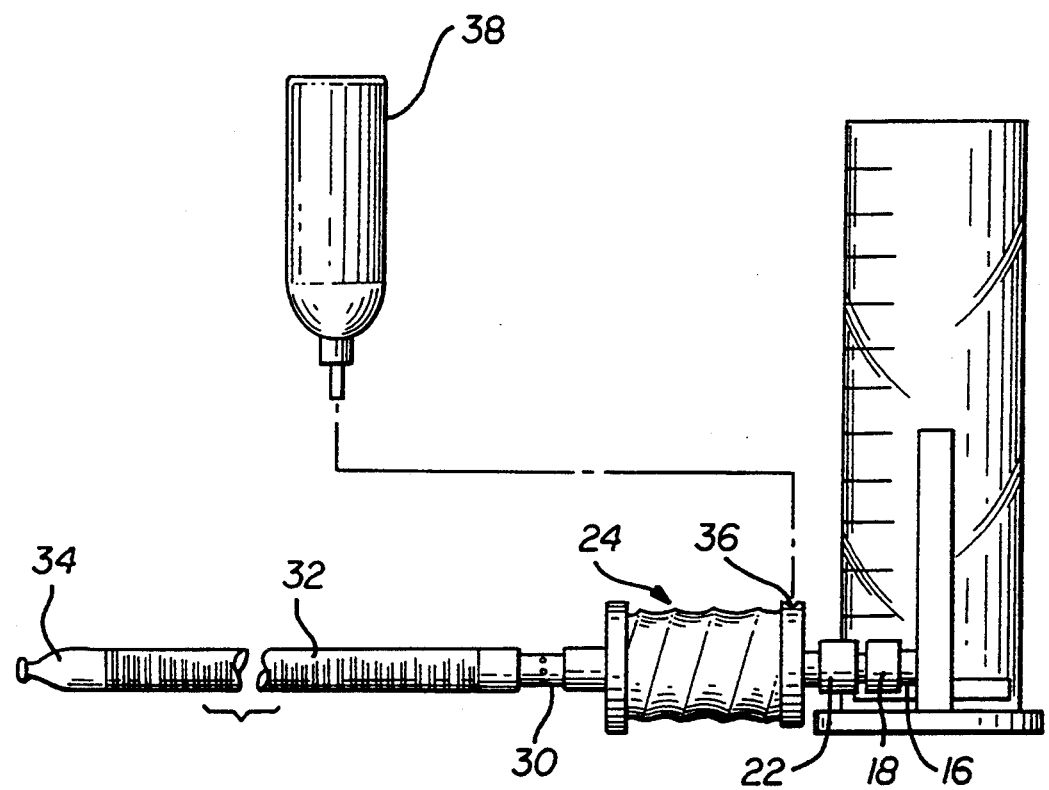
FIG. 2 is a side view of the device illustrated in the FIG. 1 in which the medication inhalation chamber is shown between the outlet of the spirometer and the elongatged hose.
Figure 3:
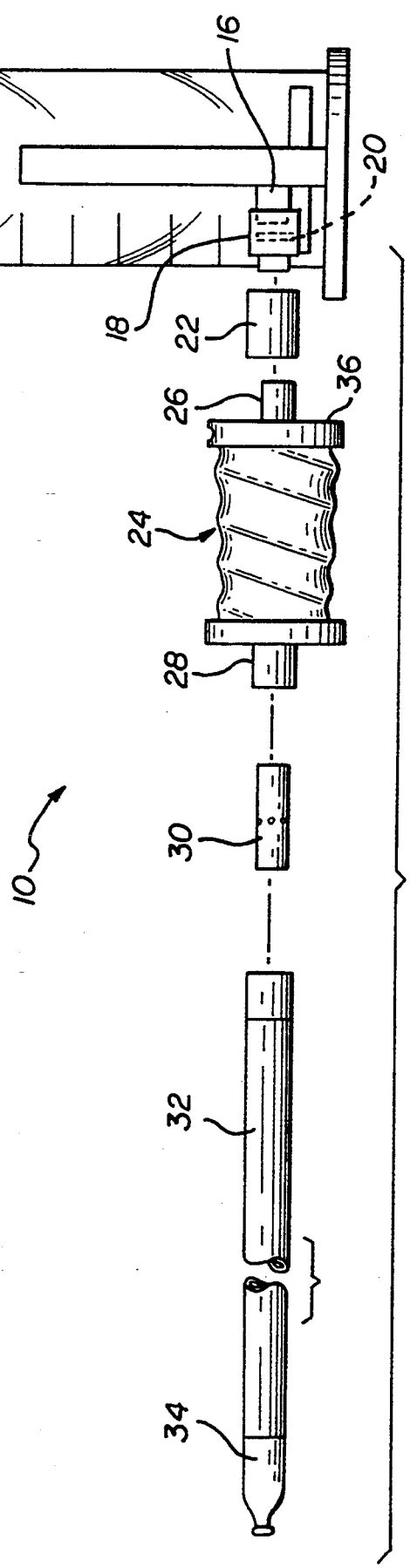
FIG. 3 is an exploded perspective view of the inhalation device of the present invention.

Referring now to the drawings, FIGS. 1-3 show an embodiment of the inhalation device 10 of the present invention. The device 10 includes an incentive spirometer 12 for indicating inhalation flow rate and total volume of the air inhaled, and for ensuring adequate breath holding time. The spirometer 12 has both an air inlet 14 and an air outlet 16. The incentive spirometer 12 of the present invention can be any of a variety of commonly available devices which provide a one-way, inspiratory airflow path with a predetermined flow resistance to the air passing therethrough. A preferable version of the invention employs the The DHD Coach ™, Model DHD 22-4000, sold by DHD Medical Products. The outlet 16 includes a unidirectional valve device 18. The valve 18 is a conventional type of flat valve having a web with openings therethrough and a flexible disk 20 which can be moved to the position shown by air flowing out of the spirometer 12 to permit the free flow thereof, but which closes the openings when air attempts to flow in the opposite direction.

The invention may also use any of a variety of well known two-way, incentive flow spirometers. A one-way valve device can be fitted to the outlet of such two-way incentive spirometers to effectively convert it into a one-way inspiratory incentive spirometer for incorporation in the present invention.

Outlet 16 of the spirometer is further provided with a coupling adapter 22 for receiving in-line a medication inhalation chamber 24. In a preferred version of the invention, the chamber 24 has a substantially cylindrical shape. A substantially cylindrical medication inhalation chamber 24 used for this preferred version is disclosed in U.S. Pat. No. 4,938,210. For the purposes of the present invention, the medication inhalation chamber can assume other shapes which provide the chamber with sufficient volume in which the misted medication can be suspended prior to inspiration and which cause larger drops or particles of aerosolized medication to "rain out." The raining out of large particles of aerosolized medication, as described below, results in a more therapeutic deposition of inspired particles.

The chamber 24 includes a first open end 26 and a second open end 28. The first open end 26 is adapted to be coupled with the outlet coupling 22 of the spirometer 12. The second open end 28, spaced from the first open end 26, is connected to another coupling 30, the other end of which is connected to the upstream end of an elongated flexible hose 32 which, together with the medication inhalation chamber 24 and coupling numbers 22 and 26, defines a passage way for the flow of air toward the patient. The elongated hose is about 6 inches in length.

Attached to the downstream end of the flexible hose 32 is a patient-engageable means 34. The patient-engageable means 34 is preferably a mouthpiece having a generally fan-shaped mouth piece portion. Other embodiments, however, of the patient-engageable means 34 may also include a standard face mask or any other suitable mouth piece configuration.

The cylindrical medication inhalation chamber 24 of the present invention also has receptable means 36 defining an inlet port located adjacent to the first open end 26, and opening into the chamber 24. The receptacle means 36 is designed to receive a metered dose inhaler (MDI) cannister 38 of aerosolized medicine 38 and to mist or dispense its aerosol medication particle contents directly into the medication inhalation chamber 24. In the present invention, aerosolized medication from an MDI device is the preferred delivery technique for reasons of dosage efficacy, reduced side effects and economy.

The device of the present invention is used for the administration of aerosolized medications selected from the group consisting of, but not limited to, bronchodilators and corticosteroids. Typical bronchodilators administered by the device include, but are not limited to, metaproterenol and albuterol. A typical corticosteroid administered by the present invention is beclomethasone. Aerosolized medications suitable for delivery by the device include antifungal medications.

Figure 4:
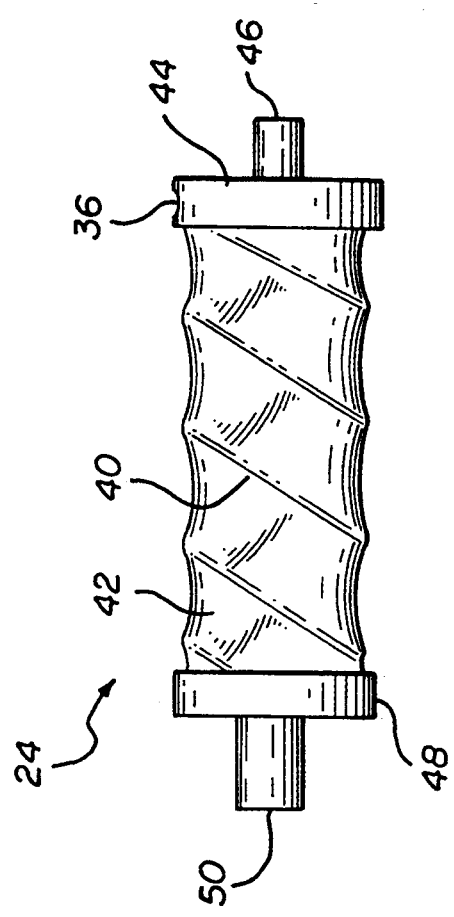
FIG. 4 is a side view of the MDI spacer device used in the present invention.

Other types of medication inhalation chamber reservoirs 24 which may be used in the present invention include extension tubes or spacers, extension tube chambers with valves, or collapsible bags, as long as these devices provide a place for a bolus of aerosol to be held prior to inhalation. However, a preferred medication inhalation chamber 24 of the present invention is the MDI spacer device which is manufactured by Monaghan Medical Corporation of Plattsburgh, N.Y. As shown in FIG. 4 the Monaghan Aerovent ™ spacer device 24 is comprised of a collapsible, cylindrical coil 40 which expands to a maximum length of approximately $4\frac{1}{2}$ inches and is approximately $1\frac{1}{2}$ inches in diameter. The coil is covered circumferentially with a clear flexible airtight plastic material 42. A first disk 44 having a centrally located opening 46 adapted to be coupled to the coupling 22 which is affixed to the outlet 16 of the spirometer 12, is securely attached to one end of the coil. This first disk 44 also includes a receptacle means 36 or port which is designed to receive the MDI container 38. A second disk 48 which also has a centrally located opening 50 is securely attached to the end of the coil located farthest from the first disk 44. The opening of the second disk 48 is designed to be connected to the coupling 30 which is connected to the hose 32. The openings 46, 50 of both the first disk 44 and the second disk 48 are coaxially aligned with each other.

The cylindrical shape of the MDI spacer device 24 is important in order to obtain the optimal aerosol particle size and is also designed to hold a bolus of aerosol in suspension prior to inhalation. The devices 10 of the present invention are preferably formed from plastics which are inert and stable and lend themselves to processing by plastic forming techniques and welding. These plastic materials, when formed, provide the break resistance, see through, self-supporting device described and claimed herein. Materials and plastics which provide the desired see through properties may be polystyrene, styrene-acrylonitrile copolymers, rigid polyvinylchloride, polymers and polycarbonate polymers.

The present invention further involves a method for administering an aerosolized medication to a subject. Typical aerosilized medications administered by this method include, but are not limited to bronchodilators, such as metaproterenol and albuterol, and corticosteoids, like beclomethasone. The method is suitable for administering any medication adapted for aerosilized delivery from an MDI, such as, antifungal medications. The method involves providing an inhalation device 10 for administering the aerosilized medication. Use of the device of the present invention, described above, is preferred for this method. The method involves training a subject or patient to breath sufficiently slowly and steadily, and to hold his breath for a sufficiently long period, to optimize his breathing control when the patient later inspires the aerosilized medication from the device 10. The incentive spirometer 12 of the device 10 is the element of the device for training the breathing of the subject.

The training conditions and breathing parameters needed for administration of aerosilized medications are well known (*Physicians Desk Reference*, 1991, Edward R. Barnhart, publisher, Medical Economics Company, Oradell, N.J.) and will not be described here in detail. When the patient achieves the desired training parameters, the method provides for the patient to manually actuate the metered dose inhaler 38 to mist the aerosolized medication into the medication inhalation chamber 24. In accordance with the breathing parameters achieved with this method using the device, the method further involves the patient inspiring the aerosolized medication misted into the chamber 24 to achieve therapeutic deposition of the aerosilized medication in the airways.

In using the device 10, the patient places his or her mouth over the mouth piece 34. The MDI dispenser 38, having already been inserted into the receptacle means 36, is manually actuated or activated to mist or dispense the aerosolized particles into the MDI spacer device, i.e. the medication inhalation chamber 24, in which the bolus of aerosol is held. As soon as the MDI aerosol has been fully dispensed into the spacer device 24, the patient is then instructed to inhale slowly and deeply, without nasal breathing, filling the lungs to the maximum extent possible on each breath. When the patient inspires, the flexible disk 20 of the valve 18 allows air to flow through the spirometer 12 and through the medication inhalation chamber (e.g. MDI spacer device) 24, thus carrying the aerosol particles through the coupling 30 and through the hose 32 and mouth piece 34 and finally into the patient's lower airways or lungs. The patient is instructed to hold his or her breath for up to 10 seconds in order to achieve optimal delivery of the aerosol to the lungs. The patient is then allowed to exhale by removing his or her mouth from the mouth piece 34. This process may be repeated as often as prescribed until the aerosolized bronchodilator achieves its desired therapeutic effect in which the bronchial tubes become unobstructed and the patient breathes easier than before treatment with the device of the present invention.

The in-line combination of the incentive spirometer 12 and medication inhalation chamber 24 adapted for receiving metered delivery of an aerosolized medication from a metered dose inhaler cannister 24 provides the advantage of eliminating the problem of precisely timing manual activation of the MDI cannister 38 with inspiration. In use by the patient, the chamber 24 holds the misted or dispensed medication prior to inhalation and achieves delivery of the proper particle size.

The substantially cylindrical medication inhalation chamber 24 combined with the incentive spirometer 12 provides the further advantage of increasing therapeutic deposition of medication to the airways by baffling out the larger particles of aerosolized medication. It is believed that large particles of aerosolized medication are less therapeutically effective than small particles. *Respiratory Care: A Guide to Clinical Practice*, 3rd Ed., Chapter 19, J. B. Lippincott Co., Philadelphia, Pa., 1991. Accordingly, the invention causes the larger particles of medication to "rain out" against the walls of the chamber instead of being delivered to the patient's airways. In that way, the patient's airways receive a deposition of smaller, therapeutic aerosolized medication particles. Use of the invention thereby achieves greater therapeutic efficacy of the medication. Accordingly, the combination of incentive spirometer 12, medication inhalation chamber 24 and metered dose inhaler delivery of aerosolized medication further increases deposition of these small aerosol particles by increasing the patient's tidal volume.

Having thus described the exemplary embodiment of the present invention, it should be noted by those skilled in the art that the within disclosures are exemplary only and have various alternatives, adoptions and modifications may be made within the scope of the present invention. Accordingly the present invention is not limited to these specific embodiments as illustrated herein, but is only limited by the following claims.

What is claimed:

1. An inhalation device for administering to a subject an aerosolized medication, comprising:
   an air flow spirometer for indicating to the subject, the subject's inhalation performance;
   a medication inhalation chamber connected at a first chamber location to said indicating means;
   a mouthpiece connected to said chamber at a chamber location spaced from said first location; and
   means for connecting a metered dose inhaler to said chamber whereby to receive into said chamber a metered dose of aerosolized medication at a location sufficiently spaced from said mouthpiece connection so as to enable the chamber to hold aerosolized medication in suspension while baffling larger particles thereof to decrease the amount thereof in said suspension, air from said spirometer flowing through said chamber whereby to deliver smaller therapeutic aerosolized medication through said mouthpiece to said subject in conjunction with operation of said spirometer.

2. The device of claim 1 wherein said medication inhalation chamber has a substantially cylindrical shape.

3. The device of claim 1 wherein said incentive spirometer is adapted for one-way inspiratory flow.

4. The device of claim 1 wherein said incentive spirometer includes a flow regulator.

5. The device of claim 1 wherein said incentive spirometer further includes indicia for measuring inspiratory volume.

6. The device of claim 1 further including a metered dose inhaler cannister containing aerosolized medication is selected from the group consisting of bronchodilators and corticosteroids.

7. The device of claim 6 wherein said bronchidilator is selected from the group consisting of metaproterenol and albuterol.

8. The device of claim 7 wherein said corticosteroid is beclomethlasone.

9. The device of claim 1 in which said spirometer provides an indication of at least one of (a) inspiratory flow rate, (b) inspiratory volume, and (c) breath holding time.

10. The device of claim 1 herein said spirometer is an incentive spirometer.

11. The device of claim 1 in which said spirometer is in line with said first location.

12. The device of claim 11 wherein said mouthpiece is connected to said chamber at a location thereon opposite from and in line with said first location.

13. An inhalation device for administering an aerosolized medication, comprising:

an incentive spirometer adapted for one-way inspiratory flow, said spirometer having an outlet and a flow regulator;

an elongated hose having a mouthpiece at a downstream end and coupling means at an upstream end; and a medication inhalation chamber having a substantially cylindrical shape, said chamber having receptacle means opening into said chamber and adapted to receive a metered dose inhaler cannister for misting aerosolized medication into said medication inhalation chamber, said chamber placed in line between said outlet and said coupling means.

14. The device of claim 13 wherein said incentive spirometer further includes indicia for measuring inspiratory volume.

15. The device of claim 13 further including a metered dose inhaler cannister containing aerosolized medication selected from the group consisting of bronchodilators and corticosteroids.

16. The device of claim 15 wherein said bronchidilator is selected from the group consisting of metaproterenol and albuterol.

17. The device of claim 15 wherein said corticosteroid is beclomethlasone.

18. A method for administering an aerosolized medication to a subject comprising the steps of:

providing an inhalation device for administering aerosolized medication, said device comprising:

an air flow spirometer for indicating to the subject, the subject's inhalation performance, a medication inhalation chamber connected at a first chamber location to said indicating means, a mouthpiece connected to said chamber at a chamber location spaced from said first location, and means for connecting a metered dose inhaler to said chamber whereby to receive into said chamber a metered dose of aerosolized medication at a location sufficiently spaced from said mouthpiece connection so as to enable the chamber to hold aerosolized medication in suspension while baffling larger particles thereof to decrease the amount thereof in suspension, air from said spirometer flowing through said chamber whereby to deliver smaller therapeutic aerosolized medication through said mouthpiece to said subject in conjunction with operation of said spirometer:

training said subject to inspire in such a way as to optimize subsequent delivery of aerosolized medication;

delivering into said receiving means of said chamber a metered dose of aerosolized medication; and having said subject inspire medication to achieve therapeutic deposition of medication in a subject's airways.

19. The method of claim 18 further including the step of providing a metered dose inhaler cannister containing aerosolized medication selected from the group consisting of bronchodilators and corticosteroids.

20. The method of claim 19 wherein said bronchidilator is selected from the group consisting of metaproterenol and albuterol.

21. The method of claim 19 wherein said corticosteroid is beclomethlasone.

22. The method of claim 18 including the step of obtaining from said spirometer an indication of at least one of (a) inspiratory flow rate, (b) inspiratory volume, and (c) breath holding time.

23. The method of claim 18 wherein said spirometer is an incentive spirometer.

24. The method of claim 18 further including the step of placing said spirometer is in line with said first location.

25. The method of claim 24 further including the step of connecting said mouthpiece to said chamber at a location thereon opposite from and in line with said first location.

* * * * *